US00PP08446P

United States Patent [19]

Pfister

[11] Patent Number: Plant 8,446

[45] Date of Patent: Nov. 2, 1993

[54] IMPATIENS PLANT NAMED PEPPERMINT RED

[76] Inventor: Brian D. Pfister, 73 Leonard Ave., Bradford, Pa. 16701

[21] Appl. No.: 919,937

[22] Filed: Jul. 27, 1992

[51] Int. Cl.[5] ..... A01H 5/00
[52] U.S. Cl. ..... Plt./87.6
[58] Field of Search ..... Plt./87.6

[56] References Cited

U.S. PATENT DOCUMENTS

P.P. 4,205 1/1978 Mikkelsen ..... Plt. 87.6

P.P. 7,690 10/1991 Cole ..... Plt. 87.6

*Primary Examiner*—James R. Feyrer
*Attorney, Agent, or Firm*—Webb, Burden, Ziesenheim & Webb

[57] ABSTRACT

A new and distinct variety of Impatiens plant named 'Peppermint Red' is characterized by the variegated foliage wherein the borders of the leaves are of yellowish-white coloration in contrast to both the darker green and washed dark green patterns of leaves and the single deep red flowers.

1 Drawing Sheet

BACKGROUND OF THE INVENTION

The present invention relates to a new and distinctive cultivar of impatiens plant known by the cultivar name 'Peppermint Red'. Walleriana 'Variegata' Impatiens is the botanical name and Impatiens or variegated impatiens is generally the commercial identification.

'Peppermint Red' was discovered in the Spring of 1989 as a sport of the variety 'Blitz' as one of about 1000 plants being grown on the same bench in the Graham's greenhouse in Bradford, Penna.

The first active asexual reproduction of 'Peppermint Red' was carried out at Graham's greenhouse in Bradford, Penna. in the Spring of 1989 and it has been demonstrated that the combination of characteristics as herein disclosed for 'Peppermint Red' are firmly fixed and are retained through successive generations of asexual reproduction.

'Peppermint Red' has not been observed under all possible environmental conditions. The phenotype may vary significantly with variations in environment such as temperature, light intensity, soil conditions, nutrient feeding and day length.

The variegation distinguishes the new impatiens from its parent, 'Blitz' and other impatiens cultivars of this type known and used in the floricultural industry within my knowledge. The variegation is a relatively thin portion which extends around the edge of the leaves and is a yellowish-white color. The darker green characteristic of the leaves of the parent 'Blitz' shades with dark and washed green patterns into the light green to white of the marginal variegated bands. This variegation is not necessarily uniform in width. It is however precisely defined and pronounced in plants grown in hot sun. It thus provides a new and unique contrast in the overall appearance of the plant with its deep red flowers giving a markedly different impression from its parent.

Flower buds are borne several to each stem and may occur in clusters at nodes. Buds of many flower clusters are of uneven maturity. Normally, several flowers are presented from a cluster at a time. There are many flowers per stem during the flowering season when the plant is used in a hanging basket. Its growth habit is indeterminate indoors but would normally be an annual in outdoor use as the plant is tender to frost.

DESCRIPTION OF THE DRAWINGS

The accompanying colored photographic drawings illustrate the new cultivar, the color being as true as possible with color illustrations of this type.

DESCRIPTION OF THE NEW PLANT

Figure 1:
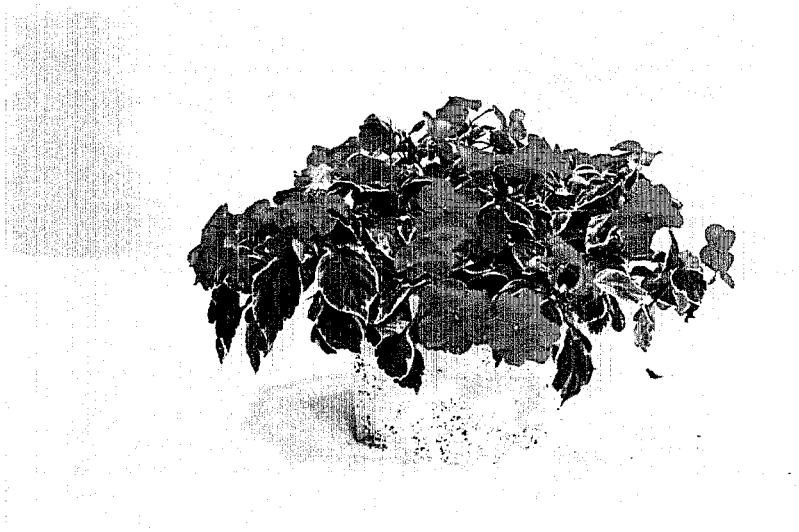
FIG. 1 is a perspective view of 'Peppermint Red' in a 7 inch pot.
Figure 2:
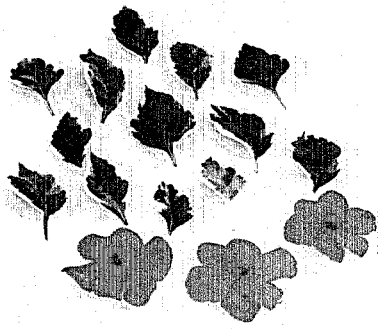
FIG. 2 is a blown up perspective showing the leaf variegation and flower color.

The following is a detailed description of 'Peppermint Red' based on plants produced at Bradford, Penna.

The plant histories were taken out-of-doors on plants blossomed under natural light. Color references are primarily to the RHS Color Chart of The Royal Horticultural Society of London.

THE PLANT

Propagation:

*Type cutting.*—Stem cutting of 2½ inches will grow to 4 inches in 2–3 weeks.

*Time to root.*—10 to 12 days.

*Rooting habit.*—Heavy, fibrous.

Form: Symmetrical; bush shaped with self-branching characteristics giving the plant a full appearance; compact.

Growth: Vigorous, mounded with flowing over the top of the foliage, self-branching, stems may trail slightly, strong growing characteristics. Grows best in partial shade. There is one leaf to each node. Each leaf has one flowering stem which may have one to five flowers depending on the time of the year. If there is more than one bud per flowering stem, male and female flowers may be present. Each flower has only one sex.

Size: When grown as single plants, with plants in full flower, the height is 12 inches from the soil line and the width or spread is also 12 inches.

Foliage:

*Internode length.*—5 mm to 3 cm.

*Leaf petiole color.*—Yellow-Green Group 147C.

*Stem color.*—Yellow-Green Group 147B.

*Leaf shape.*—Mostly oblique.

*Leaf size.*—2–4 inches in height depending on maturity and 1½ to 1¾ inches in width.

*Leaf margins.*—Undulate.

*Leaf texture.*—Glabrous.

*Venation.*—Pinnate.

*Leaf color.*—Variegation occurs on all leaves and is precisely defined although it does not extend throughout the surface of the leaf. The variegation is a relatively thin portion which extends around the edge of the leaf and is yellowish-white in color. Variegation is more pronounced in plants grown in hot sun. Dark inner green Grayed/Green Group 189A; Second green Grayed/Green Group 194B; Third green Grayed/Green Group 195D; Outer green, if present, Grayed/Green Group 191C; Outer margin Yellow/White Group 158A; Underside green matches Grayed/Green Group 191B; Underside yellow-white same as top yellow-white matches Yellow/White Group 158A. The underneath side of the leaf has blemishes like a birthmark, color Purple Violet Group 82D. Blemishes vary from leaf to leaf. A given leaf may have different blemishes with there being no given pattern or size. These blemishes blend in with the green of the leaf. There is reddish tint at leaf nodes, the color being Red Group 44C.

Leaves: New leaf development up to ½ inch size Green Group 137A. Yellow-white edge new leaf development Yellow/White Gropu 158A.

THE FLOWER

Habit: Flowers continuously from leaf whorl and are located above the leaf whorl. It can have from 2 to 7 flowers on one flowering stem. Flowers are single. All flowers have five petals with a double petal on top. The top petal is heart shaped. The other four petals have slight indentations at the apex of each petal which are drawn slightly backwards. Flowers last 4–5 days and plant flowers continuously once started.

Born: Several to each stem in irregular clusters. Staminate and pistillate flowers on the same stem.

Quantity: Moderate, outdoors and in greenhouses.

Continuity: An annual, one season.

Size: 1½ to 2 inches in diameter.

Color: Red Group 45B. Stays the same throughout the flowering stages. Underside of the flower Red Group 40C. Bud color at ¼ size Red Group 36C.

Plant stem: Yellow/Green Group 148D.

Flower stem: Yellow/Green Group 148C.

Sepals: None.

Spur: A longish curved spur extends on the bottom side of the flower. Its color is Red Group 44C. The spur grows from the center of the flower to the outside edge of the petal. On a 4.5 cm flower, the spur is 2.5 cm long.

REPRODUCTIVE ORGANS

Seed: Seeding is present. Progeny testing has shown that seeds from 'Peppermint Red' mainly reproduce parent plant 'Blitz'. A few exceptions have produced variegated plants. The male and female organs are attached directly to the flower center with the anther being tight against the flower. The stamen appears to have no filament. The anthers are greenish in color with the pollen being yellowish white. The stigma is whitish in color and variegation lines appear on the ovaries.

I claim:

1. A new and distinct variety of impatiens plant named 'Peppermint Red' as illustrated and described.

* * * * *